(12) United States Patent
Fleig et al.

(10) Patent No.: US 12,115,030 B2
(45) Date of Patent: Oct. 15, 2024

(54) DETACHABLE TRACKING REFERENCE ARRAY

(71) Applicant: Brainlab AG, Munich (DE)

(72) Inventors: Oliver Fleig, Baldham (DE); Anna Wiedenmann, Feldkirchen (DE); Melanie Stulpe, Rosenheim (DE); Tobias Neun, Woerth (DE)

(73) Assignee: Brainlab AG, Munich (DE)

( * ) Notice: Subject to any disclaimer, the term of this patent is extended or adjusted under 35 U.S.C. 154(b) by 613 days.

(21) Appl. No.: 15/116,474

(22) PCT Filed: Feb. 7, 2014

(86) PCT No.: PCT/EP2014/052441
§ 371 (c)(1),
(2) Date: Aug. 3, 2016

(87) PCT Pub. No.: WO2015/117665
PCT Pub. Date: Aug. 13, 2015

(65) Prior Publication Data
US 2017/0007353 A1    Jan. 12, 2017

(51) Int. Cl.
A61B 90/00    (2016.01)
A61B 5/06    (2006.01)
A61B 17/00    (2006.01)

(52) U.S. Cl.
CPC ............. A61B 90/39 (2016.02); A61B 5/065 (2013.01); A61B 2017/00477 (2013.01); A61B 2017/00876 (2013.01); A61B 2090/3983 (2016.02)

(58) Field of Classification Search
CPC . A61B 90/39; A61B 5/065; A61B 2090/3983; A61B 2017/00876;
(Continued)

(56) References Cited

U.S. PATENT DOCUMENTS 6,227,853 B1 * 5/2001 Hansen ................. A61C 1/148
279/128
8,098,544 B2 * 1/2012 Roche ..................... G01S 15/88
367/124
(Continued)

FOREIGN PATENT DOCUMENTS

FR    2799361 A1 *    4/2001    ............. A61B 90/39
WO    2014005225 A1    1/2014
WO    WO-2015115807 A1 *    8/2015    ............. A61B 17/16

OTHER PUBLICATIONS

"The Electromagnet", https://www.electronics-tutorials.ws/electromagnetism/electromagnets.html, part of content cited appearing in May 2018 update, page first documented on Jan. 20, 2010 (Year: 2010).*

(Continued)

Primary Examiner — Joseph M Santos Rodriguez
Assistant Examiner — Amy Shafqat
(74) Attorney, Agent, or Firm — Tucker Ellis LLP

(57) ABSTRACT

The invention relates to a tracking reference, comprising: a reference array (1) featuring a positionally fixed arrangement of at least two tracking markers (3); and an interface (4A) for detachably coupling the reference array (1) to a base member (2), wherein the interface (4A) comprises at least one supporting surface (5) for contacting the base member (2), wherein the interface (4A) comprises magnetic means (6) which generate a force at the reference array, wherein the force (F) is directed away from the supporting surface (5).

11 Claims, 3 Drawing Sheets

(58) Field of Classification Search
CPC .......... A61B 2017/00477; A61B 19/00; A61B 2017/00486; A61B 2017/0046; A61B 2017/00473; A61B 2017/0042; A61B 2017/00424; A61B 2090/3991; A61B 2034/2072; A61B 17/809; A61B 2090/3916; A61B 2090/363; A61B 90/36; A61B 17/1757; A61B 17/1775; A61B 17/1789; A61B 17/1742; A61B 17/1767; A61B 17/1746; A61B 17/175; A61B 17/1753; A61B 17/8894; A61B 17/1764; A61B 17/1792; A61B 17/52; A61B 5/1114; A61B 6/547; A61B 90/50; A61B 90/57; A61B 2090/571; A61B 2560/0431; A61B 2560/04; A61B 2017/00455; A61B 2017/00831; A61B 2017/00464; A61B 2034/2057; A61B 2034/2055; A61B 2034/2046; A61B 34/20; A61B 2034/2068; A61B 2034/207; A61B 34/00; A61F 2/46; A61F 2002/4641; A61F 2/4644; A61F 2/4637; A61F 2002/4638; A61F 2002/4632; A61F 2002/4633; A61F 2002/4622; A61F 2/4603; A61F 2002/30696; A61F 2002/285

See application file for complete search history.

(56) References Cited

U.S. PATENT DOCUMENTS

| | | | | |
|---|---|---|---|---|
| 8,421,642 | B1 * | 4/2013 | McIntosh | A61B 5/0002 340/686.1 |
| 8,638,296 | B1 * | 1/2014 | McIntosh | G06F 3/017 345/158 |
| 8,834,488 | B2 * | 9/2014 | Farritor | A61B 1/00158 606/130 |
| 8,968,332 | B2 * | 3/2015 | Farritor | A61B 1/00158 606/130 |
| 9,011,448 | B2 * | 4/2015 | Roche | A61B 8/58 606/86 R |
| 9,033,957 | B2 * | 5/2015 | Cadeddu | A61B 17/0469 606/1 |
| 2005/0085822 | A1 * | 4/2005 | Thornberry | A61B 34/20 606/86 R |
| 2005/0119639 | A1 * | 6/2005 | McCombs | A61B 90/39 606/1 |
| 2006/0142774 | A1 * | 6/2006 | Metzger | A61B 17/155 606/79 |
| 2007/0167703 | A1 * | 7/2007 | Sherman | A61B 5/06 600/407 |
| 2007/0287910 | A1 * | 12/2007 | Stallings | A61B 90/39 600/426 |
| 2008/0086150 | A1 * | 4/2008 | Mathis | A61B 90/50 606/130 |
| 2008/0097496 | A1 * | 4/2008 | Chang | A61B 17/064 606/157 |
| 2009/0306499 | A1 | 12/2009 | Van Vorhis et al. | |
| 2010/0160932 | A1 * | 6/2010 | Gschwandtner | A61B 90/39 606/139 |
| 2010/0249581 | A1 * | 9/2010 | McCombs | A61B 90/36 600/426 |
| 2011/0004259 | A1 * | 1/2011 | Stallings | A61B 90/39 606/86 R |
| 2011/0263971 | A1 | 10/2011 | Constantinos | |
| 2014/0303631 | A1 * | 10/2014 | Thornberry | A61F 2/4609 606/91 |
| 2016/0113730 | A1 * | 4/2016 | Lightcap | A61B 34/20 701/500 |
| 2016/0199069 | A1 * | 7/2016 | Kehres | A61B 17/1617 606/80 |
| 2017/0071691 | A1 * | 3/2017 | Crawford | A61B 90/96 |
| 2017/0252109 | A1 * | 9/2017 | Yang | A61B 5/064 |
| 2018/0000554 | A1 * | 1/2018 | Paradis | A61F 2/4657 |
| 2018/0193097 | A1 * | 7/2018 | Mclachlin | A61B 34/20 |
| 2018/0280092 | A1 * | 10/2018 | Van Beek | A61B 90/39 |
| 2019/0046252 | A1 * | 2/2019 | Skinlo | A61B 17/8852 |

OTHER PUBLICATIONS

International Search Report, PCT/EP2014/052441, Mailed on: Oct. 7, 2014, 4 pages.

* cited by examiner

DETACHABLE TRACKING REFERENCE ARRAY

The invention relates to the general technical field of tracking references used to determine the spatial position of medical instruments and anatomical structures.

Tracking reference arrays are used in order to allow surgical tracking systems to track the spatial position of anatomical structures and medical instruments to which the tracking references are secured, by detecting tracking markers associated with the tracking reference array. Since these tracking markers are arranged in rigid and specific patterns relative to each other, the tracking system can determine the exact spatial position of the corresponding tracking reference and consequently also the spatial position of an anatomical structure or medical instrument to which the tracking reference is secured.

One example of a known tracking reference comprises a base member which is attached to an anatomical structure or an instrument by suitable means such as bone screws or clamps, and a reference array which normally comprises three tracking markers which can be detected by a medical tracking system. Common tracking references can also comprise mechanical means which allow the reference array to be releasably attached to the base member, such as for example resiliently articulated elements which are provided in such a way that the reference array can be snap-fitted to the base member and consequently to the anatomical structure or medical instrument.

Such mechanical solutions are however cumbersome, expensive to produce and difficult to sterilise.

US 2010/0249581 A1 shows a tracking reference comprising a fault interface which holds the reference array on the base, for example by means of a friction fit. The fault interface can also comprise a connection aid which provides for magnetic attraction, in order to additionally support the connection between the reference array and the base.

It is the object of the present invention to provide a tracking reference which is inexpensive to produce and easy to use and suitable for a wide range of different applications.

This object is achieved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said embodiment.

The tracking reference according to the invention comprises a reference array featuring a positionally fixed arrangement of at least two tracking markers, and an interface for detachably coupling the reference array to a base member. The interface also comprises at least one supporting surface for contacting the base member, and magnetic means which generate a force at the reference array, wherein the force is directed away from the supporting surface.

The tracking markers are designed to be detected by a tracking system (for example, a camera or an ultrasound receiver or analytical devices such as CT or MRI devices) in such a way that their spatial position (i.e. their spatial location and/or alignment) can be ascertained. The detection device is in particular part of a navigation system. The markers can be active markers which for example emit electromagnetic radiation and/or waves in the infrared, visible and/or ultraviolet spectrum range. The markers can also however be passive markers which for example reflect electromagnetic radiation and/or waves in the infrared, visible and/or ultraviolet spectrum range or which block x-ray radiation. To this end, the markers can be provided with a surface which has corresponding reflective properties or can be made of metal in order to block the x-ray radiation. It is also possible for the markers to reflect and/or emit electromagnetic radiation and/or waves in the radio frequency range or at ultrasound wavelengths. The markers preferably have a spherical and/or spheroid shape and can therefore be referred as marker spheres. They can however also exhibit a cornered shape, for example a cubic shape.

In other words, the tracking reference comprises a first section which includes an array of at least two tracking markers in a predetermined spatial arrangement, and a second section which extends from the first section and comprises an interface which can be formed so as to mate with a complementarily shaped interface on a base member which is in turn attached to an anatomical structure or a medical instrument. In order to provide sufficient support for the reference array, the reference array interface comprises at least one supporting surface which can be formed so as to exactly fit at least one complementarily shaped surface of the base member interface. The interface also comprises magnetic means for attaching the reference array to an object which allows the magnetic means to generate a force at the reference array. A complementarily shaped interface of a base member can for example also comprise magnetic means in order to allow the reference array to be attached to the base member by means of a force fit generated by the magnetic means. However, it is also possible to attach the reference array to any suitable object which can cause the magnetic means of the reference array interface to be attracted to the object.

The magnetic means of the reference array interface can be placed within the interface in such a way that the magnetic force is transferred predominantly via one supporting surface; alternatively or additionally, the magnetic means can even constitute a supporting surface. In order to allow the reference array to be attached to an object, the supporting surface should be a surface which is situated at an outermost position on the interface, facing away from the tracking marker array.

In accordance with one preferred embodiment of the present invention, the magnetic means are formed by at least one permanent magnet and/or at least one electromagnet, such that the reference array can be attached to any object which exhibits ferromagnetic properties.

In accordance with another preferred embodiment of the present invention, the tracking reference comprises not only a reference array as described above but also a base member featuring an interface which corresponds to the reference array interface and also magnetic means which generate a force at the reference array, wherein the force is directed away from the supporting surface. If the base member interface is provided with a permanent magnet or electromagnet, then the reference array interface itself need not comprise a permanent magnet or electromagnet, i.e. need only comprise a ferromagnetic material. Providing a permanent magnet or an electromagnet on the reference array interface is however preferred, since this allows the reference array to be attached to any object which exhibits ferromagnetic properties, in addition to the base member.

In accordance with another preferred embodiment of the present invention, the attachment connection between the reference array and the base member is established and maintained solely by the magnetic means of the reference array and base member, respectively. In other words, no other means are provided, either on the reference array or on the base member, which adhere the reference array to the base member.

The base member can also comprise means for attaching the base member to a medical instrument or part of a patient's body, such as for example bone screws or clamps.

It is however also conceivable for the base member to comprise a tool section, in particular at a predetermined position with respect to its interface. Such a tool section can for example be selected from the group consisting of a pointer tip, a cutting blade and a machining tool. In accordance with this preferred embodiment of the present invention, the tool section can consist of any medical instrument, in particular any hand-held medical instrument, which is to be tracked within a surgical environment. If the tool section is situated at a predetermined spatial position with respect to the interface and consequently also with respect to the tracking markers of the reference array, there is no need to calibrate the surgical instrument, since the position of the tool section relative to the tracking markers is already known.

In accordance with another preferred embodiment of the present invention, at least one supporting surface defines a predetermined spatial position relative to the arrangement of at least two tracking markers. A plane comprising a spatial position which can be easily determined by determining the spatial position of each of the reference array tracking markers can for example comprise a flat or planar supporting surface of the reference array interface. If a supporting surface comprises a predetermined spatial position with respect to the tracking markers, and in particular if this surface is at an outermost or protruding position on the tracking reference interface, then the spatial orientation of flat ferromagnetic instruments or instrument parts can be determined simply by attaching the reference array, together with its magnetic means, to the instrument. Two of the three tracking markers of each of the reference arrays can for example exhibit the same distance from the supporting surface plane, while the third tracking markers exhibit the same distance from the other two tracking markers and define a direction perpendicular to said plane.

In accordance with another preferred embodiment of the present invention, the interfaces of the reference array and the base member are formed so as to define a predetermined spatial position of said reference array relative to said base member when coupled to said base member. In order to obtain such a predetermined spatial position of the reference array relative to the base member, a plurality of supporting surfaces can be provided which restrict any movement of the reference array relative to the base member, except for such movement as is necessary for attaching the reference array to the base member and detaching it from the base member; this can in particular be a movement perpendicular to a flat supporting surface formed by the magnetic means. Corresponding flat surfaces can for example be provided on the reference array interface and the base member interface which allow translational movement parallel to the plane of the flat surfaces and rotational movement about a rotational axis which is perpendicular to said plane. Additional complementarily shaped supporting surfaces which extend perpendicular to the flat surfaces can be provided on the circumference of each interface in order to prevent such movement.

It is however also conceivable for the interfaces of the reference array and the base member to be formed so as to allow a predefined movement of the reference array relative to the base member while it is coupled to the base member. This could for example be accomplished using two corresponding flat supporting surfaces and two corresponding circumferential supporting surfaces, as described above, with the circumferential surfaces forming a rotationally symmetrical profile, for example a cylindrical surface.

In the embodiments described above, the magnetic force can be transferred predominantly through the flat surfaces, which can then be formed from a magnetic material. The interfaces can contact each other via a cylindrical surface, wherein the force generated by the magnetic means is directed parallel to the axis of symmetry of the cylindrical surface.

The interface of the base member is preferably formed by a recess in the base member, while the reference array interface is formed by a complementarily shaped protrusion, wherein the interfaces can be configured to either allow or restrict any desired movement of the reference array and base member relative to each other. It is therefore also for example conceivable for the interfaces to form a ball joint or swivel joint.

Since the interface is inexpensive to produce, it is possible to design the reference array and/or base member as disposable products which are for example made from a plastic material and do not need to be sterilised after use.

In the following, the invention is described with reference to the enclosed figures which represent preferred embodiments of the invention. The scope of the invention is not however limited to the specific features disclosed in the figures.

Figure 1:
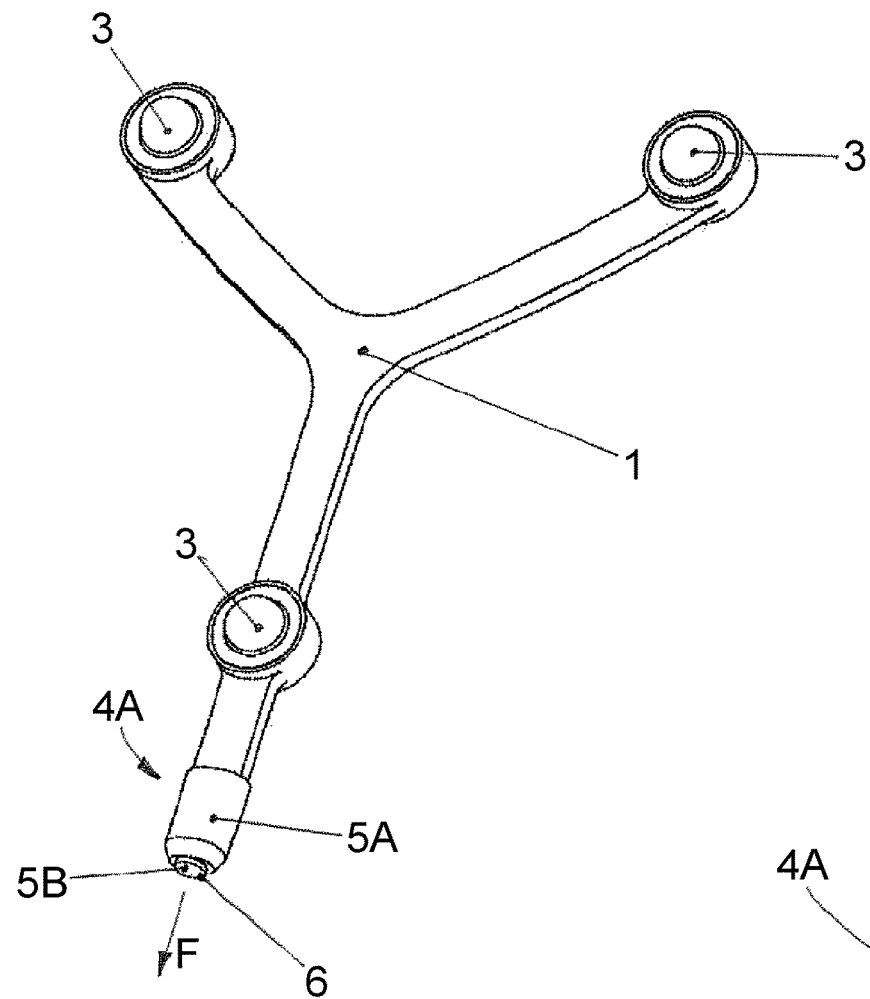
FIG. 1 shows a reference array in accordance with the invention.
Figure 2:
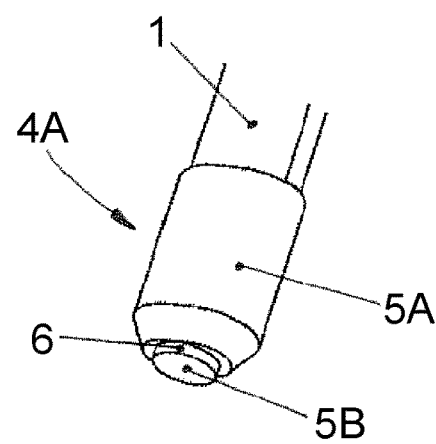
FIG. 2 shows an enlarged view of the reference array interface in accordance with the invention.

The reference array 1 shown in FIG. 1 comprises a marker section featuring three spherical tracking markers 3 which are designed to be detected by an optical medical tracking system. The reference array 1 also comprises an interface 4A which extends from the marker section and comprises two supporting surfaces 5A and 5B and a magnetic means 6. As can also be seen in FIG. 2, one of the supporting surfaces 5A forms a cylindrical outer surface, while the other supporting surface 5B forms a flat, end-facing surface which extending perpendicular to the axis of rotational symmetry of the cylindrical surface. The flat, end-facing supporting surface is formed by the surface of a permanent magnet 6 which protrudes from the interface 4A and generates a force F at the reference array 1 which is directed perpendicular to and away from the flat surface 5B, such that by means of the permanent magnet 6, the reference array 1 is "drawn" to any ferromagnetic material brought into the more immediate vicinity of the permanent magnet 6.

Figure 3:
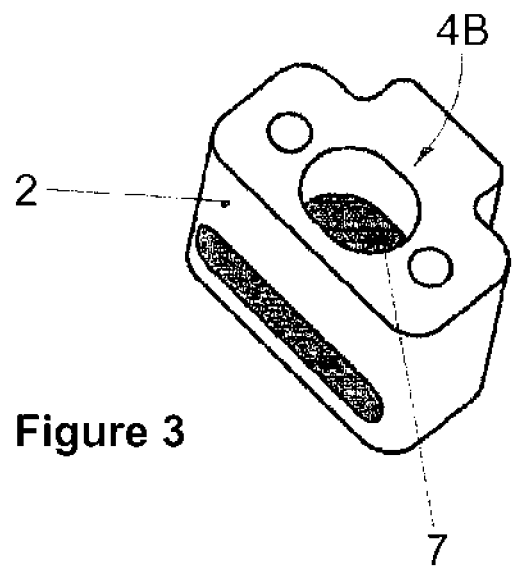
FIG. 3 shows a base member in accordance with the invention.

FIG. 3 shows a base member 2 in accordance with the invention, comprising an interface 4B which forms a recess within the body of the base member 2. The bottom of the recess is formed as a flat surface 7 which exhibits a magnetic means, for example a ferromagnetic material or a permanent magnet, wherein the walls of the recess extend perpendicular to the flat bottom of the recess and form an oval circumferential surface.

If a complementarily shaped, i.e. likewise oval interface 4A of a reference array is inserted into the recessed interface 4B of the base member 2, the permanent magnet 6 will be drawn towards the ferromagnetic material, thereby holding the reference array 1 firmly in place on the base member 2. Since the side walls of the interface form an oval surface, it is clear that a complementarily shaped, i.e. oval outer surface 5A of a reference array interface 4A will be prevented from rotating within the recessed interface 4B, thereby preventing any relative movement between the reference array 1 and the base member 2. If, however, a cylindrical or otherwise rotationally symmetrical outer surface 5A of a reference array interface 4A is dimensioned so as to be small enough to be inserted into the interface 4B, then it is equally clear that the interfaces 4A and 4B would then allow a rotational movement about a rotational axis which is perpendicular to the flat surfaces 5B and 7. A set of tracking references 1 can thus be provided which comprises both reference arrays 1 which can be rotated relative to the base member 2 and reference arrays 1 which are prevented from rotating or indeed moving in any way relative to the base member 2.

Figure 4:
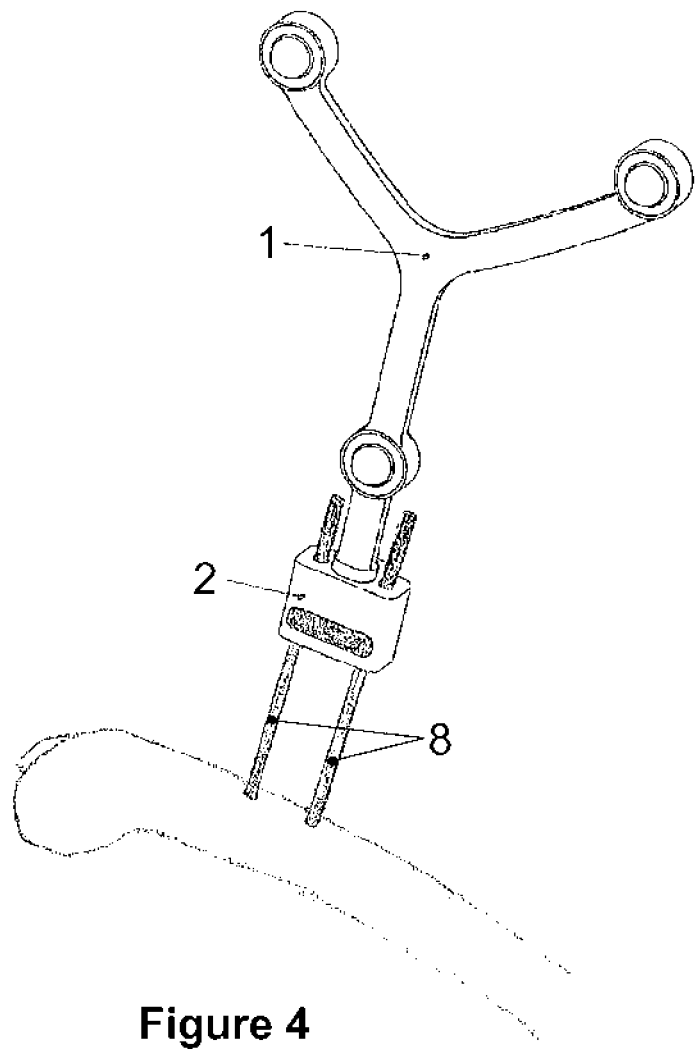
FIG. 4 shows a tracking reference in accordance with the invention, comprising a reference array and a base member which is secured to an anatomical structure.

FIG. 4 shows a base member 2 secured to a bone by means of two bone screws 8 which extend through recesses of the base member 2 (and which are not provided with reference numerals in FIGS. 3 and 4). The base member 2 comprises an interface 4B such as is shown in FIG. 3, while the reference array 1 comprises an interface 4A which exhibits a circumferential surface 5A which exactly matches the circumferential surface of the interface 4B, such that the reference array 1 is prevented from moving in any way relative to the base member 2. With the reference array 1 rigidly attached to the base member 2 and therefore the bone in this way, it is possible to determine and track its exact spatial position (i.e. spatial location and spatial orientation) by determining and tracking the spatial location of each of the tracking markers 3 by means of a medical tracking system.

Figure 5:
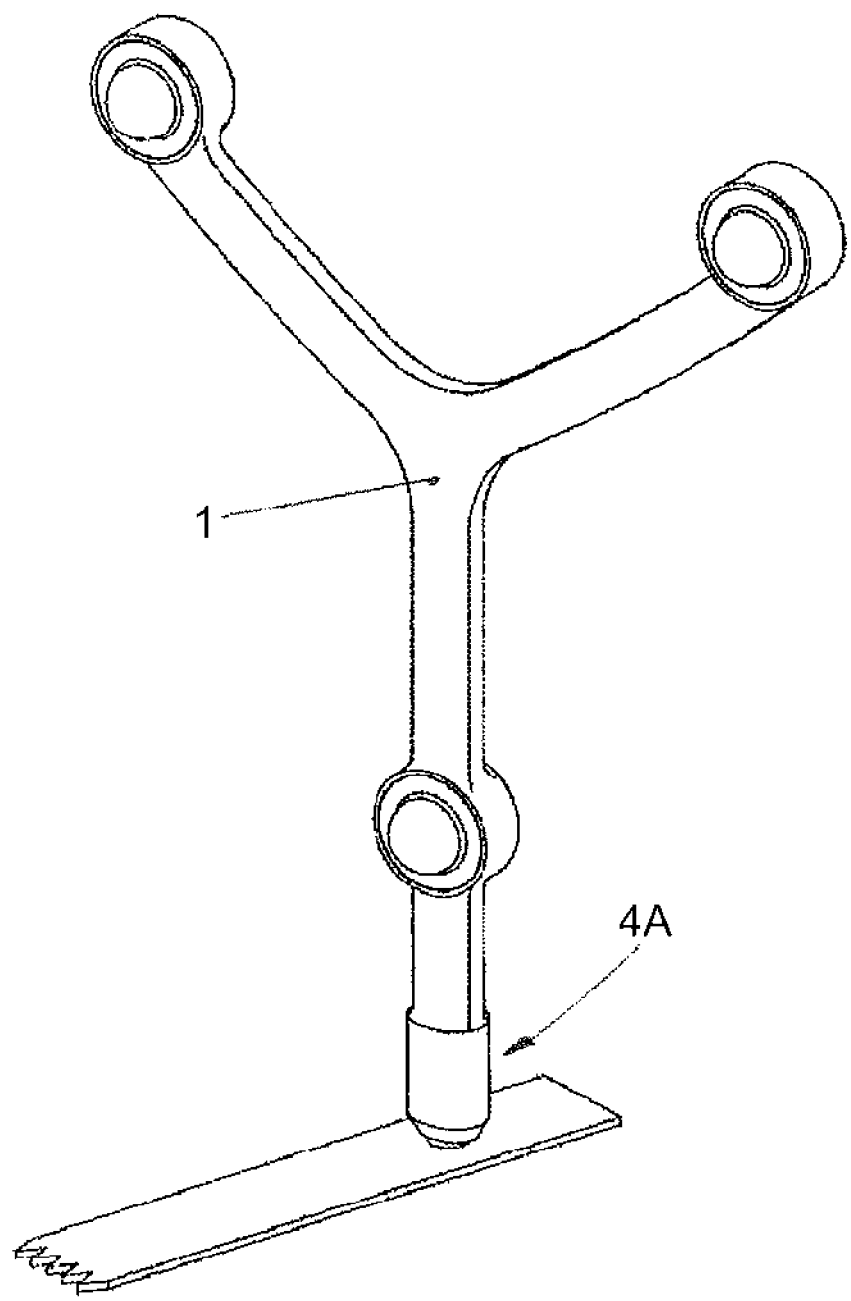
FIG. 5 shows a reference array in accordance with the invention, attached to a flat ferromagnetic object.

FIG. 5 shows another application of the present invention, namely that of determining the plane of a flat, ferromagnetic object such as a saw blade or a chisel, simply by placing the flat permanent magnet of the reference array 1 onto the surface of the flat, ferromagnetic object. Since the spatial position of the supporting surface 5B which comprises the magnetic means 6 is known relative to the reference array 1, the plane of the flat object is also immediately known.

The invention claimed is:

1. A tracking reference device for attachment to a base member or a surface, comprising:
   a reference array having at least three positionally fixed tracking markers, the reference array further having at least three arms, wherein a respective tracking marker of the at least three positionally fixed tracking markers is located on a respective arm of the at least three arms; and
   an interface portion provided at an end of one arm of the at least three arms, the interface portion configured to detachably couple the tracking reference device to at least one of the base member or a surface, wherein the interface portion includes:
      a magnet protruding from a distal end of the interface portion and causing an attractive force to detachably couple the tracking reference device to the at least one of the base member or the surface;
      a cylindrical section extending along the arm and between a corresponding tracking marker located on the arm and the end of the arm, the cylindrical section having a shape corresponding to a complimentary shaped recess of the base member; and
      a taper section disposed between the magnet and the cylindrical section, the taper section having a first radius adjacent to the cylindrical portion and a second radius adjacent to the magnet, wherein the first radius is larger than the second radius,
   wherein, when the tracking reference device is coupled to the base member, the magnet and at least a portion of the cylindrical section are received within the complimentary recess of the base member.

2. The tracking reference device of claim 1, wherein the base member includes an interface that is complementarily shaped with respect to the interface portion, and magnetic means that generate a force at the interface.

3. The tracking reference device of claim 2, wherein the magnetic means of the base member is formed by a ferromagnetic material.

4. The tracking reference device of claim 2, wherein the base member includes a coupling that attaches the base member to a medical instrument or to a part of an associated patient's body.

5. The tracking reference device of claim 2, wherein a form of the interface portion of the tracking reference device and the interface of the base member defines a predetermined spatial position of the reference array relative to the base member when coupled to the base member.

6. The tracking reference device of claim 2, wherein the interface portion of the tracking reference device and the interface of the base member contact each other via a cylindrical surface.

7. The tracking reference device of claim 2, wherein at least the reference array or the base member is designed as disposable.

8. The tracking reference device of claim 2, wherein the base member includes a tool section at a predetermined position with respect to the interface of the base member.

9. The tracking reference device of claim 8, wherein the tool section is selected from a group consisting of a pointer tip, a cutting blade and a machining tool.

10. The tracking reference device of claim 2, wherein a form of the interface portion of the tracking reference device and the interface of the base member is configured to allow a predefined movement of the reference array relative to the base member while it is coupled to the base member.

11. The tracking reference device of claim 10, wherein the predefined movement comprises a translational or a rotational movement.

* * * * *